(12) United States Patent
Jayaseelan et al.

(10) Patent No.: US 9,588,044 B2
(45) Date of Patent: Mar. 7, 2017

(54) INLINE BURIED METAL VOID DETECTION BY SURFACE PLASMON RESONANCE (SPR)

(71) Applicant: GLOBALFOUNDRIES Inc., Grand Cayman (KY)

(72) Inventors: Sabarinath Jayaseelan, Niskayuna, NY (US); Suraj Kumar Patil, Ballston Lake, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 70 days.

(21) Appl. No.: 14/800,940

(22) Filed: Jul. 16, 2015

(65) Prior Publication Data
US 2017/0016822 A1    Jan. 19, 2017

(51) Int. Cl.
*G01N 21/552* (2014.01)
*G01N 21/95* (2006.01)

(52) U.S. Cl.
CPC ....... *G01N 21/553* (2013.01); *G01N 21/9501* (2013.01)

(58) Field of Classification Search
CPC .. G01N 21/552; G01N 21/553; G01N 21/554; G01N 21/658; G01N 21/88; G01N 21/8806; G01N 21/892; G01N 21/9501; G01N 21/9505; G01N 2021/8918; G01N 2021/8925; G01N 2021/5903; G01N 2021/8845; G01N 2021/887; G01N 2021/8924; G01N 2021/8927; G01N 2021/8928; G01N 2021/8962;
(Continued)

(56) References Cited

U.S. PATENT DOCUMENTS 9,194,811 B1 * 11/2015 Zhao .................. G01N 21/8806
2007/0279635 A1 * 12/2007 Wu ........................ G01B 11/14
356/445
(Continued)

FOREIGN PATENT DOCUMENTS

JP    10012681 A  *  1/1998

OTHER PUBLICATIONS

Romero et al., "Plasmonics in buried structures", vol. 17, No. 21, Optics Express, Optical Society of America, Published Oct. 2, 2009, retrieved on Aug. 18, 2015 from https://www.osapublishing.org/view_article.cfm?gotourl=https%3A%2F%2Fwww%2Eosapublishing%2Eorg%2FDirectPDFAccess%2F8030ED19-DC6E-99A1-E0EC629317C873_186450%2Foe-17-21-18866%2Epdf%3Fda%3D1%26id%3D186450%26seq%3D0%26mobile%3Dno&org=, 12 Pages.
(Continued)

*Primary Examiner* — Gordon J Stock, Jr.
(74) *Attorney, Agent, or Firm* — Ditthavong & Steiner, P.C.

(57) ABSTRACT

A method and apparatus are provided for using SPR to detect buried voids in a semiconductor wafer inline post metal deposition. Embodiments include forming a first, a second, and a third metal structure in a first, a second, and a third adjacent die of a wafer; performing a SPR on the first, second, and third metal structures inline; detecting a first, a second, and a third SPR wavelength corresponding to the first, second, and third metal structures, respectively; comparing a difference between the first SPR wavelength and the second SPR wavelength and a difference between the third SPR wavelength and the first SPR wavelength against a threshold value; and determining a presence or an absence of a buried void in the first metal structure based on the comparison.

20 Claims, 3 Drawing Sheets

(58) Field of Classification Search
CPC ....... G01N 2021/8965; G01N 21/8914; G01N 21/8921; G01N 21/8922; G01N 21/894; G01N 21/896; G01N 21/898; H01L 21/67242; H01L 21/67253; H01L 21/67288; H01L 22/00; H01L 22/10; H01L 22/12; H01L 22/30
See application file for complete search history.

(56) References Cited

U.S. PATENT DOCUMENTS

| | | | | |
|---|---|---|---|---|
| 2008/0266568 | A1* | 10/2008 | VanWiggeren | G01N 21/553 356/445 |
| 2014/0139837 | A1* | 5/2014 | Kim | G01N 21/11 356/445 |
| 2015/0377795 | A1* | 12/2015 | Zhao | G01N 21/33 250/372 |

OTHER PUBLICATIONS

Amrani et al., "Plasmon-Polaritons and Their Use in Optical Sub-Wavelength. Event of Copper and Silver", International Journal of Recent advances in Physics (IJRAP) vol. 2, No. 2, May 2013, retrieved on Aug. 18, 2015 from http://wireilla.com/physics/ijrap/papers/2213ijrap02.pdf, 7 Pages.

Teperik et al., "Strong coupling of light to flat metals via a buried nanovoid lattice: the interplay of localized and free plasmons", Mar. 6, 2006, vol. 14, No. 5, Optics Express, Optical Society of America, retrieved on Aug. 18, 2015 from http://www.np.phy.cam.ac.uk/uploads/2006/optexp06-voidtheory.pdf, 8 Pages.

Wassel et al., "Towards Chip-Scale Plasmonic Interconnects", Workshop on the Interaction between Nanophotonic Devices and Systems (MICRO Workshop) Dec. 2010, retrieved on Aug. 18, 2015 from http://www.csl.cornell.edu/winds2010/abstracts/wassel-winds2010.pdf, 2 Pages.

Rephaeli et al., "Tungsten black absorber for solar light with wide angular operation range", Applied Physics Letters 92, 2008, retrieved on Aug. 18, 2015 from http://web.stanford.edu/group/fan/publication/Rephaeli_APL_92_211107_2008.pdf, 3 Pages.

\* cited by examiner

INLINE BURIED METAL VOID DETECTION BY SURFACE PLASMON RESONANCE (SPR)

TECHNICAL FIELD

The present disclosure relates to a manufacture of semiconductor devices such as integrated circuits. The present disclosure is particularly applicable to detecting defective metal components on a semiconductor wafer.

BACKGROUND

During deposition of metal on a semiconductor wafer, for example, by chemical vapor deposition (CVD), physical vapor deposition (PVD), electro-chemical plating (ECP), or electroless plating (ELP), improper fill or voids may be formed in vias or trenches due to various factors such as improper mass transport, reaction kinetics, a contaminated substrate, etc. The presence of a buried void in a semiconductor wafer, e.g., in a trench silicide structure, may cause serious reliability concerns. However, buried voids cannot currently be detected by surface scans, e.g., bright field inspection (BFI), scanning electron microscope (SEM), etc. In addition, inspection of a wafer by electron beam (Ebeam) is also challenging. Such defects are currently only highlighted post-production by failure analysis (FA) cuts of the wafer or by electrical test (ET) data showing either open or increased contact resistance.

A need therefore exists for methodology and an apparatus enabling detection of buried voids in a semiconductor wafer inline post metal deposition.

SUMMARY

An aspect of the present disclosure is a method for detecting buried voids in a semiconductor wafer inline post metal deposition using surface plasmon resonance (SPR).

Another aspect of the present disclosure is an apparatus including a modified SPR instrument capable of detecting buried voids on a semiconductor wafer.

Additional aspects and other features of the present disclosure will be set forth in the description which follows and in part will be apparent to those having ordinary skill in the art upon examination of the following or may be learned from the practice of the present disclosure. The advantages of the present disclosure may be realized and obtained as particularly pointed out in the appended claims.

According to the present disclosure, some technical effects may be achieved in part by a method including: forming a first, a second, and a third metal structure in a first, a second, and a third adjacent die of a wafer; performing a SPR on the first, second, and third metal structures inline; detecting a first, a second, and a third SPR wavelength corresponding to the first, second, and third metal structures, respectively; comparing a difference between the first SPR wavelength and the second SPR wavelength and a difference between the third SPR wavelength and the first SPR wavelength against a threshold value; and determining a presence or an absence of a buried void in the first metal structure based on the comparison.

Aspects of the present disclosure include forming the first, second, and third structures of tungsten (W), copper (Cu), titanium (Ti), titanium nitride (TiN), cobalt (Co), aluminum (Al), tantalum (Ta), and/or tantalum nitride (TaN). Other aspects include the first, second, and third metal structures being formed as vias, trenches, or gates. Further aspects include forming the first, second, and third metal structures by: CVD, atomic layer deposition (ALD), physical vapor deposition (PVD), electro-chemical plating (ECP), and/or electroless plating (ELP). Additional aspects include the buried void being formed from oxide, air, or an organic residue. Another aspect includes reworking the first metal structure if the comparison reveals the presence of the buried void. Other aspects include reworking the first metal structure by: annealing the first metal structure; and performing a remote plasma treatment. Further aspects include reworking the first metal structure by: annealing the first metal structure without performing a remote plasma treatment. Additional aspects include testing the reworking of the first metal structure by: performing a SPR on the reworked first metal structure; and comparing a difference between a SPR wavelength corresponding to the reworked first metal structure and the second SPR wavelength and a difference between the third SPR wavelength and the SPR wavelength corresponding to the reworked first metal structure against the threshold value.

Another aspect of the present disclosure is an apparatus including: a modified SPR instrument capable of detecting buried voids on a semiconductor wafer, the modified SPR instrument having at least a light source, a prism, and a detector; and a semiconductor wafer having a plurality of dies, the plurality of dies being placed relative to the SPR instrument at an angle incident to the light source.

Aspects of the apparatus include the apparatus being configured to perform a SPR on three identically formed metal structures, each structure being formed in a neighboring die within the plurality of dies. Other aspects include the SPR being performed inline. Further aspects include one of the three identically formed metal structures being a target structure and a remaining two of the three identically formed metal structures being a first and a second reference structure. Additional aspects include the detector being configured to detect a SPR wavelength corresponding to the target structure and a first and a second SPR wavelength corresponding to the first and second reference structures, respectively. Another aspect includes a comparison module being configured to compare a difference between the detected SPR wavelength corresponding to the target structure and the first SPR wavelength and a difference between the second SPR wavelength and the detected SPR wavelength corresponding to the target structure against a threshold value. Other aspects include the comparison module being configured to determine an absence or presence of a buried void in the target structure based on the comparison.

A further aspect of the present disclosure is a method including: providing a wafer having a first, a second, and a third metal structure formed in a first, a second, and a third adjacent die of the wafer, respectively; performing a SPR on the first, second, and third metal structures; detecting a first SPR wavelength corresponding to the first metal structure, a second SPR wavelength corresponding to the second metal structure, and a third SPR wavelength corresponding to the third metal structure; comparing a difference between the first SPR wavelength and the second SPR wavelength and a difference between the third SPR wavelength and the first SPR wavelength against a threshold value; and determining whether the first metal structure was formed improperly based on the comparison.

Aspects of the present disclosure include reworking the first metal structure or discarding the wafer if an improper formation is determined. Other aspects include reworking the first metal structure by: annealing the first metal structure with or without a remote plasma treatment. Further aspects include testing the reworking by: performing a SPR on the reworked first metal structure; and comparing a difference between a SPR wavelength corresponding to the reworked first metal structure and the second SPR wavelength and a difference between the third SPR wavelength and the SPR wavelength corresponding to the reworked first metal structure against the threshold value.

Additional aspects and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments. In addition, unless otherwise indicated, all numbers expressing quantities, ratios, and numerical properties of ingredients, reaction conditions, and so forth used in the specification and claims are to be understood as being modified in all instances by the term "about."

The present disclosure addresses and solves the current problem of an inability to detect buried voids in a semiconductor wafer inline post metal deposition attendant upon the manufacture of integrated circuits.

Methodology in accordance with embodiments of the present disclosure includes forming a first, a second, and a third metal structure in a first, a second, and a third adjacent die of a wafer. A SPR is performed on the first, second, and third metal structures inline. A first, a second, and a third SPR wavelength corresponding to the first, second, and third metal structures, respectively, are detected. A difference between the first SPR wavelength and the second SPR wavelength and a difference between the third SPR wavelength and the first SPR wavelength are compared against a threshold value and a presence or an absence of a buried void in the first metal structure is determined based on the comparison.

Still other aspects, features, and technical effects will be readily apparent to those skilled in this art from the following detailed description, wherein preferred embodiments are shown and described, simply by way of illustration of the best mode contemplated. The disclosure is capable of other and different embodiments, and its several details are capable of modifications in various obvious respects. Accordingly, the drawings and description are to be regarded as illustrative in nature, and not as restrictive.

Figure 1:
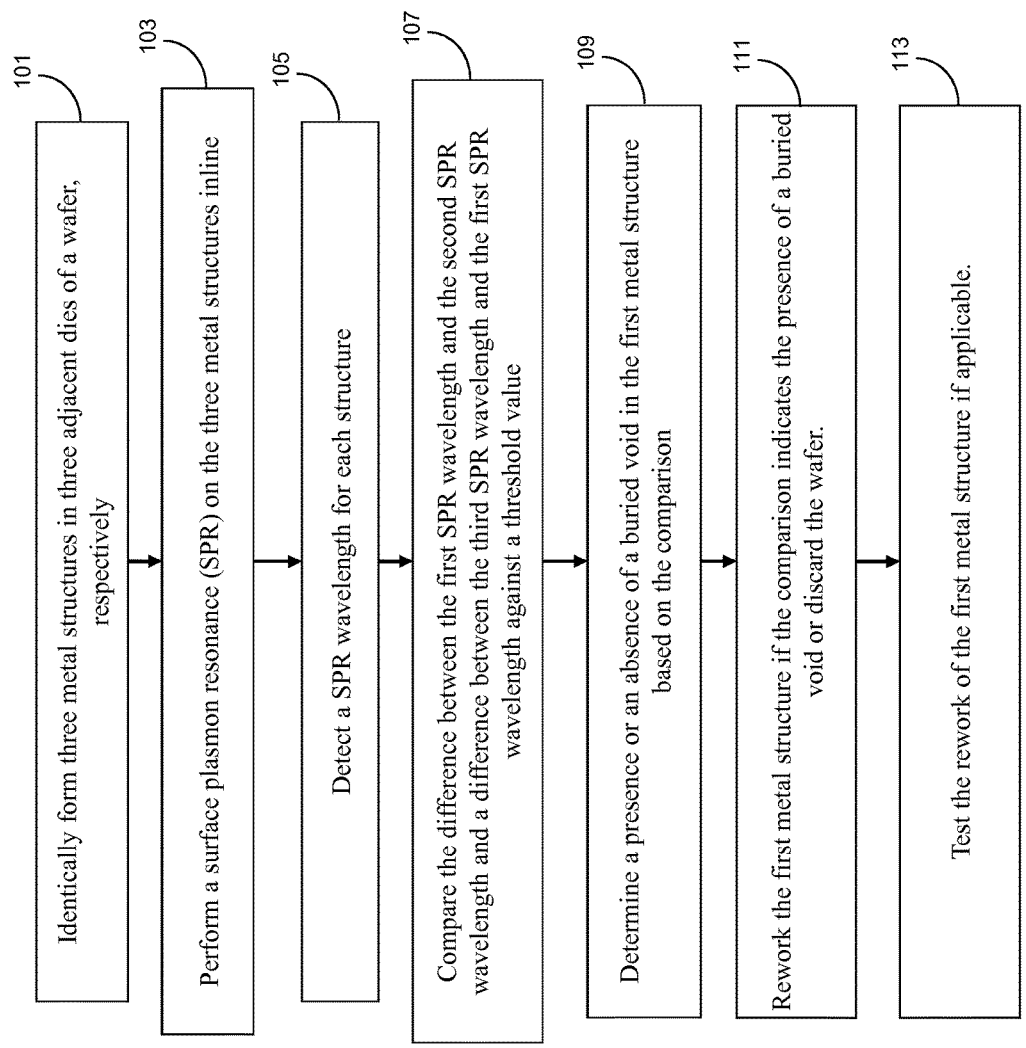
FIG. 1 illustrates an inline SPR process flow for detecting buried voids in a semiconductor wafer post metal deposition, in accordance with an exemplary embodiment.
Figure 2:
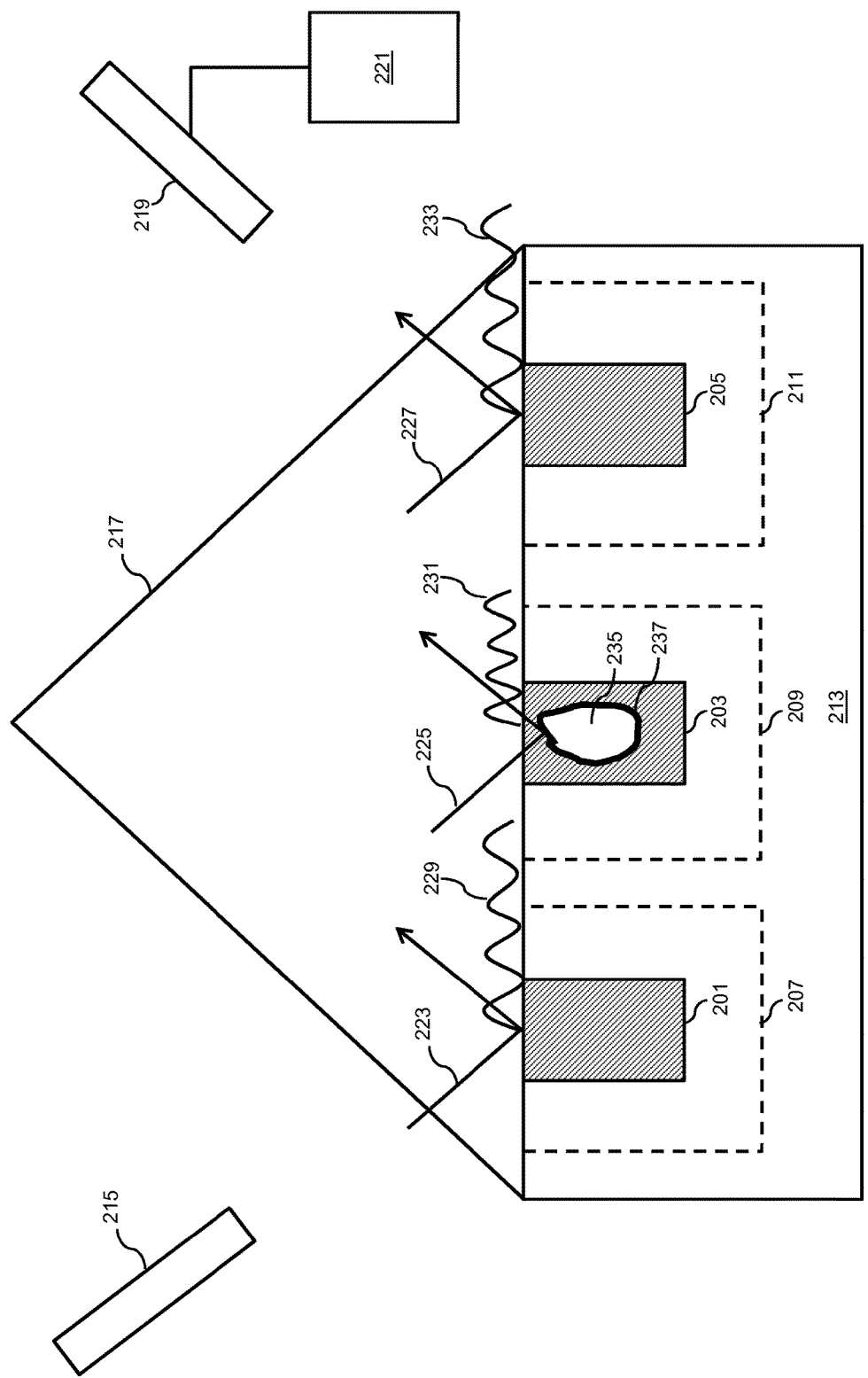
FIG. 2 schematically illustrates an example detection of a buried void in a semiconductor wafer post metal deposition based on the inline SPR process flow, in accordance with an exemplary embodiment.

FIG. 1 illustrates an inline SPR detection process flow for detecting buried voids in a semiconductor wafer post metal deposition, in accordance with an exemplary embodiment, and FIG. 2 schematically illustrates an example detection of a buried void in a semiconductor wafer post metal deposition based on the inline SPR flow, in accordance with an exemplary embodiment. In step 101, three identically formed metal structures, e.g., vias, trenches, or gates, are respectively formed in three neighboring dies of a semiconductor wafer. For example, the metal structures 201, 203, and 205 of FIG. 2 may be formed in dies 207, 209, and 211 of the semiconductor wafer 213. The metal structures 201, 203, and 205 may be formed, for example, of W, Cu, Ti, TiN, Co, Al, Ta, TaN, and/or any other type of metal deposition. The metal structures 201, 203, and 205 may also be formed, for example, by CVD, ALD, PVD, ECP, and/or ELP.

In step 103, a SPR is performed on all three metal structures inline. SPR occurs when a light beam is incident on a metal-dielectric interface, and surface plasmon polaritons (SPP) or electromagnetic waves propagate along the surface of the metal. The resulting wavelength/resonance changes for different materials and, therefore, will change for an improperly filled or voided trench compared to a filled trench. The relationship between the wavelength, the dielectric constant of the material, and the magnetic permeability of the material is as follows:

$$K(\omega) = \frac{\omega}{c} \sqrt{\frac{\varepsilon_1 \varepsilon_2 \mu_1 \mu_2}{\varepsilon_1 \mu_1 + \varepsilon_2 \mu_2}},$$

wherein $\omega$ is the wave number, $\in$ is the dielectric constant, and $\mu$ is the magnetic permeability of the material. Accordingly, a SPR may be performed on the metal structures 201, 203, and 205 using a modified SPR instrument capable of detecting buried voids on a semiconductor wafer including a light source 215, a prism 217, and a detector 219. In this example, the detector 219 is connected to a comparison module 221. The SPR may be performed, for example, by directing the light source 215, e.g., ultraviolet (UV) through visible light (Vis), at an angle incident to the surface of the metal structures 201, 203, and 205. The particular light source 215 used for the SPR may be tunable based on the type of material the SPR will be used for. For example, the light waves 223, 225, and 227 may be directed at the metal structures 201, 203, and 205, respectively.

In step 105, a SPR wavelength corresponding to each of the three metal structures is detected by the detector 219. For example, the detector 219 may detect the SPR wavelengths 229, 231, and 233 resulting from light waves 223, 225, and 227 being directed at the metal structures 201, 203, and 205, respectively. In this example, the metal structure 203 is the target structure and the metal structures 201 and 205 are used as reference structures. Ideally, the SPR wavelengths 229 and 233 will be close to identical and the SPR wavelength 231 will be relatively lower or higher depending on the type of void present in the metal structure 203.

In step 107, the difference ($W_B-W_A$) between the resulting SPR wavelength for the target structure ($W_B$) and the resulting SPR wavelength for one of the reference structures ($W_A$) and the difference ($W_C-W_B$) between the resulting SPR wavelength for the other reference structure ($W_C$) and the resulting SPR wavelength for the target structure ($W_B$) are compared against a threshold value, e.g., by the comparison module 221. The threshold value is essentially an acceptable deviation or delta between the value of a surface plasmon for a completely filled structure and the value of a surface plasmon for a similar voided structure, e.g., similar in terms of design and dimensions. The threshold value may be affected by the type of material, volume of material, type of surrounding material, type of void, and the size of the void. For example, the comparison may be as follows: $W_B-W_A>K<W_C-W_B$ (K–Threshold Value) wherein $$K(\omega) = \frac{\omega}{c} \sqrt{\frac{\varepsilon_1 \varepsilon_2 \mu_1 \mu_2}{\varepsilon_1 \mu_1 + \varepsilon_2 \mu_2}},$$

and wherein ω is the wave number, ∈ is the dielectric constant, and μ is the magnetic permeability of the material.

In step 109, a presence or an absence of a buried void in the target structure can be determined based on the comparison of SPR wavelengths against the target value. For example, the comparison module 221 can compare the difference between the SPR wavelength 231 and the SPR wavelength 229 and the difference between the SPR wavelength 233 and the SPR wavelength 231 against a threshold value. Based on the comparison, the comparison module 221, for example, can determine that in this example, the metal structure 203 has a buried void 235 and a metal-dielectric interface 237. The buried void 235 may be formed, for example, of oxide, air, or an organic material. Further, the buried void 235 may be formed, for example, during metal deposition by CVD due to the influence of various factors such as improper mass transport, reaction kinetics, contaminated substrate, etc. In other words, the comparison module 221, for example, may determine the presence of the void 235 in the metal structure 203 based on the fact that the wavelength/resonance 231 for the metal structure 203 is a threshold value different than the wavelengths/resonances 229 and 233 for the metal structures 201 and 205, respectively.

In step 111, where the presence of a buried void is detected, the target structure, e.g., the metal structure 203, may be reworked to remove the void or if reworking is not possible and/or the defectiveness is above a certain target level, then the semiconductor wafer may be discarded to save on further processing costs and resource utilization. For example, the metal structure 203 may be annealed with or without a remote plasma treatment depending on the severity and/or nature of the void 235 or the wafer 213 may be discarded.

In step 113, if the target structure, e.g., the metal structure 203, is reworked to attempt to remove the void 235, the rework may be tested. For example, the reworking of the metal structure 203 may be tested by performing a SPR on the reworked metal structure 203. There is a good possibility that during rework (wherever applicable) new residue/particles may be introduced, but generally it is expected that such residue/particles will be at a lower level and that the SPR scan of the reworked structure will mainly be a confirmation scan to confirm that the rework helped. For example, the comparison module 221 can compare the difference between the SPR wavelength corresponding to the reworked metal structure 203 and the SPR wavelength 229 and the difference between the SPR wavelength 233 and the SPR wavelength corresponding to the reworked metal structure 203 against the threshold value to determine whether the void 235 has now been removed as a result of the rework, e.g., by annealing and/or by a remote plasma treatment.

Figure 3:
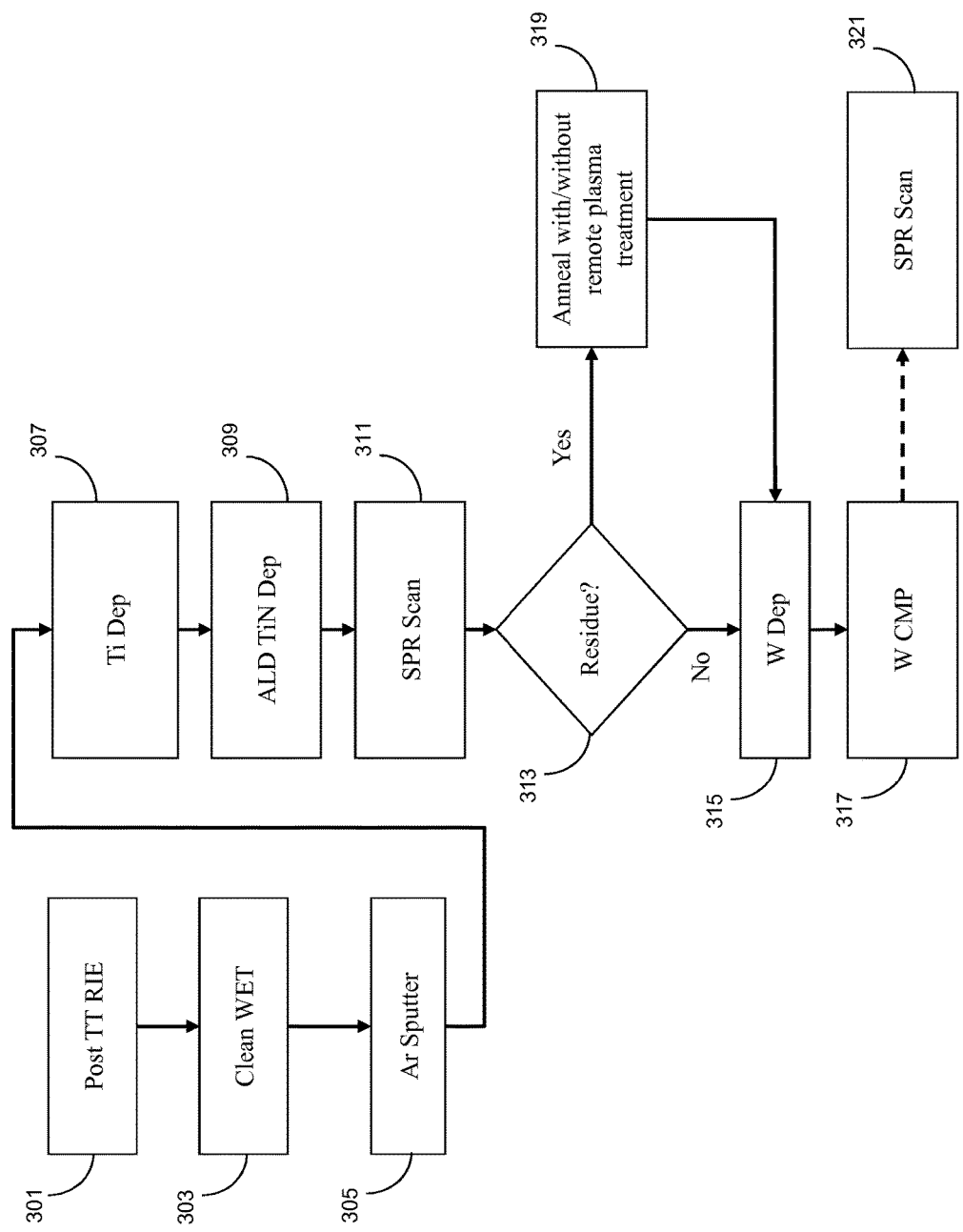
FIG. 3 illustrates an example inline SPR process flow for detecting buried voids in a semiconductor wafer post metal deposition, in accordance with an exemplary embodiment.

FIG. 3 illustrates an example SPR process flow for detecting buried voids in a semiconductor wafer post metal deposition, in accordance with an exemplary embodiment. In step 301, a trench contact (TT) is formed, e.g., by reactive ion etching (RIE), in a semiconductor wafer. In step 303, the trench contact is cleaned, e.g., by wet etching (WET). In step 305, the trench contact is further cleaned, e.g., by argon (AR) sputter. In step 307, Ti is deposited in the trench contact. In step 309, TiN is deposited, e.g., by ALD, over the Ti in the trench forming a Ti/TiN contact structure. In step 311, a SPR is performed on the Ti/TiN structure and on two other identically formed structures in neighboring dies of the wafer. In this example, the Ti/TiN contact structure is the target structure and the two other identically formed structures are the reference structures. In step 313, the SPR wavelengths corresponding to the target structure and the reference structures are detected. A difference between the target SPR wavelength and a reference SPR wavelength and a difference between the other reference SPR wavelength and the target SPR wavelength are compared against a threshold value. If the difference between the target SPR wavelength and the reference SPR wavelengths is less than the threshold value, i.e., the Ti/TiN structure does not have a void or residue, W is deposited over the Ti/TiN structure in step 315 and then planarized, e.g., by chemical mechanical polishing (CMP), in step 317.

However, if the difference between the target SPR wavelength and the reference SPR wavelengths is greater than the threshold value, i.e., the Ti/TiN structure has a void or residue, e.g., as a result of the Ti/TiN structure's formation, then the Ti/TiN structure is reworked in step 319. For example, the Ti/TiN structure may be annealed with or without a remote plasma treatment depending on the severity and/or nature of the void or the wafer may be discarded. In step 321, the rework of step 319 may be tested by performing a SPR scan of the reworked Ti/TiN structure and then comparing the differences between the reworked SPR wavelength and the reference SPR wavelengths against the threshold value. As previously stated, there is a good possibility that during rework (step 319) new residue/particles may be introduced, but generally it is expected that such residues/particles will be at a lower level.

The embodiments of the present disclosure can achieve several technical effects including inline detection for any type of buried voids, improved reliability of dies/final product due to early detection, higher sensitivity since SPR is currently used for nanoscale and below levels, and an improved deposition process due to the early detection. Embodiments of the present disclosure enjoy utility in various industrial applications as, for example, microprocessors, smart phones, mobile phones, cellular handsets, set-top boxes, DVD recorders and players, automotive navigation, printers and peripherals, networking and telecom equipment, gaming systems, and digital cameras. The present disclosure therefore enjoys industrial application for detecting any type of buried voids in semiconductor devices.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. A method comprising:
    forming a first, a second, and a third metal structure in a first, a second, and a third adjacent die of a wafer;
    performing a surface plasmon resonance (SPR) on the first, second, and third metal structures inline;
    detecting a first, a second, and a third SPR wavelength corresponding to the first, second, and third metal structures, respectively;
    comparing a difference between the first SPR wavelength and the second SPR wavelength and a difference between the third SPR wavelength and the first SPR wavelength against a threshold value; and
    determining a presence or an absence of a buried void in the first metal structure based on the comparison.

2. The method according to claim 1, comprising forming the first, second, and third structures of tungsten (W), copper (Cu), titanium (Ti), titanium nitride (TiN), cobalt (Co), aluminum (Al), tantalum (Ta), and/or tantalum nitride (TaN).

3. The method according to claim 1, wherein the first, second, and third metal structures comprise vias, trenches, or gates.

4. The method according to claim 1, comprising forming the first, second, and third metal structures by:
    chemical vapor deposition (CVD), atomic layer deposition (ALD), physical vapor deposition (PVD), electrochemical plating (ECP), and/or electroless plating (ELP).

5. The method according to claim 1, wherein the buried void comprises oxide, air, or an organic residue.

6. The method according to claim 1, further comprising reworking the first metal structure if the comparison reveals the presence of the buried void.

7. The method according to claim 6, comprising reworking the first metal structure by:
    annealing the first metal structure; and
    performing a remote plasma treatment.

8. The method according to claim 6, comprising reworking the first metal structure by:
    annealing the first metal structure without performing a remote plasma treatment.

9. The method according to claim 6, comprising testing the reworking of the first metal structure by:
    performing a SPR on the reworked first metal structure; and
    comparing a difference between a SPR wavelength corresponding to the reworked first metal structure and the second SPR wavelength and a difference between the third SPR wavelength and the SPR wavelength corresponding to the reworked first metal structure against the threshold value.

10. An apparatus comprising:
    a modified surface plasmon resonance (SPR) instrument capable of detecting buried voids on a semiconductor wafer, the modified SPR instrument having at least a light source, a prism, and a detector; and
    a semiconductor wafer having a plurality of dies, the plurality of dies being placed relative to the SPR instrument at an angle incident to the light source.

11. The apparatus according to claim 10, wherein the apparatus is configured to perform a SPR on three identically formed metal structures, each structure being formed in a neighboring die within the plurality of dies.

12. The apparatus according to claim 11, wherein the SPR is performed inline.

13. The apparatus according to claim 11, wherein one of the three identically formed metal structures is a target structure and a remaining two of the three identically formed metal structures are a first and a second reference structure.

14. The apparatus according to claim 13, wherein the detector is configured to detect a SPR wavelength corresponding to the target structure and a first and a second SPR wavelength corresponding to the first and second reference structures, respectively.

15. The apparatus according to claim 14, further comprising a comparison module configured to compare a difference between the detected SPR wavelength corresponding to the target structure and the first SPR wavelength and a difference between the second SPR wavelength and the detected SPR wavelength corresponding to the target structure against a threshold value.

16. The apparatus according to claim 15, wherein the comparison module is configured to determine an absence or presence of a buried void in the target structure based on the comparison.

17. A method comprising:
    providing a wafer having a first, a second, and a third metal structure formed in a first, a second, and a third adjacent die of the wafer, respectively;
    performing a surface plasmon resonance (SPR) on the first, second, and third metal structures;
    detecting a first SPR wavelength corresponding to the first metal structure, a second SPR wavelength corresponding to the second metal structure, and a third SPR wavelength corresponding to the third metal structure;
    comparing a difference between the first SPR wavelength and the second SPR wavelength and a difference between the first SPR wavelength and the third SPR wavelength against a threshold value; and
    determining whether the first metal structure was formed improperly based on the comparison.

18. The method according to claim 17, further comprising reworking the first metal structure or discarding the wafer if an improper formation is determined.

19. The method according to claim 18, further comprising reworking the first metal structure by:
    annealing the first metal structure with or without a remote plasma treatment.

20. The method according to claim 19, comprising testing the reworking by:
    performing a SPR on the reworked first metal structure; and
    comparing a difference between a SPR wavelength corresponding to the reworked first metal structure and the second SPR wavelength and a difference between the SPR wavelength corresponding to the reworked first metal structure and the third SPR wavelength against the threshold value.

* * * * *